United States Patent [19]

Young et al.

[11] Patent Number: 4,551,167
[45] Date of Patent: Nov. 5, 1985

[54] METHOD OF SOIL NITRIFICATION INHIBITION BY APPLICATION OF A STABILIZED FUMIGANT COMPOSITION

[75] Inventors: Donald C. Young, Fullerton; James A. Green, II, Chino, both of Calif.

[73] Assignee: Union Oil Company of California, Los Angeles, Calif.

[21] Appl. No.: 633,014

[22] Filed: Jul. 20, 1984

[51] Int. Cl.$^4$ .............................................. C05G 3/08
[52] U.S. Cl. ........................................ 71/64.1; 71/27; 71/902; 71/903; 47/58; 424/161
[58] Field of Search ................... 71/7, 902, 64.1, 1, 71/27, 903, 904; 47/58

[56] References Cited

PUBLICATIONS

CA99(17):138732r, Yanover et al., "Effect of Carbon Disulfide . . . Soil", 1983.
CA87(3):16857s, Singh et al., "Effect of Pyridine . . . Medium", 1973.

*Primary Examiner*—Ferris H. Lander
*Attorney, Agent, or Firm*—Dean Sandford; Gregory F. Wirzbicki; Robert A. Franks

[57] ABSTRACT

A stabilized fumigant composition comprises an aqueous solution containing up to about fifty percent by weight of a solute which comprises ammonia, hydrogen sulfide and carbon disulfide. Elemental sulfur can also be a component of the solute. One preferred composition comprises a solution wherein the molarity of hydrogen sulfide is about 1.5 times the molarity of carbon disulfide, and is about one-half the molarity of ammonia, and wherein the molarity of sulfur is about 1.6 times the molarity of carbon disulfide.

The composition decomposes in a soil environment to form sources of available plant nutrients, including ammonia, hydrogen sulfide and sulfur, and carbon disulfide which inhibits nitrification and decreases the nematode population. Nutrient content can be enhanced by the addition of, for example, ammonia, ammonium nitrate, urea and mixtures thereof to the formed composition.

The composition can also be decomposed by dilution or heat application, or both, to yield its components for non-soil fumigation uses.

17 Claims, No Drawings

METHOD OF SOIL NITRIFICATION INHIBITION BY APPLICATION OF A STABILIZED FUMIGANT COMPOSITION

This application is a division of application Ser. No. 315,492, filed Oct. 27, 1981, now U.S. Pat. No. 4,476,113.

BACKGROUND OF THE INVENTION

1. Field of the Invention

This invention relates to a stabilized fumigant composition for controlling fungi, insects, rodents, nematodes and weeds, and for inhibiting nitrification in a soil environment, which composition comprises an aqueous solution of ammonia, hydrogen sulfide, carbon disulfide and, optionally, elemental sulfur.

2. Description of the Art

Among the more economically serious plant parasites are nematodes, roundworms comprising as many as 10,000 species, of which at least 150 are known to adversely affect plant life. Plant parasitic nematodes have been known since about 1750. Most of the nematodes which cause crop damage do so by feeding on plant roots, and therefore are found primarily in the upper few inches of soil in the roots or in close proximity to the roots. Nematode feeding causes hypertrophy or gall formation, and the evidence of heavy infestation is plant stunting, pale foliage, wilting, and even plant death in extreme cases.

Virtually all of the world's crops and ornamental plants can be attacked by parasitic nematodes. Important destructive nematode species include the root knot nematodes which are hosted by tomatoes, alfalfa, cotton, corn, potatoes, citrus and many other crops, the golden nematode of potatoes, the sugar beet cyst nematode and the citrus nematode. These, and a few other species, are described in "The Soil Pest Complex", *Agricultural and Food Chemistry*, Vol. 3, pages 202–205 (1955). Also described therein is a further complication resulting from nematode infestation, namely a lowered resistance to the effects of plant attack by bacteria and pathogenic soil fungi.

Except for small volumes of soil which can be sterilized, it has not been found possible to eliminate nematodes. Parasite populations can, however, be kept at levels which economically permit agricultural operations by soil fumigation, crop rotation using non-hosting plant varieties, and (to a much lesser extent) the development of plants which are resistant to infestation. In many instances, control of nematodes is achieved only by combinations of these techniques, and most control programs have proven quite costly.

The process of soil fumigation requires the movement of gaseous chemicals through the soil which is treated, and the readily apparent necessity for a sufficient concentration of gas at a given temperature and pressure condition to be lethal to the pest which would be controlled. Volatility of the chemical agent is critical to successful fumigation, since a very volatile substance will disperse too readily and not develop an effective concentration exept for locations very close to the point of introduction to the soil. Substances having a very low volatility are also undesirable, since they will not disperse in the soil, and will be effective only at locations near the point of introduction.

Carbon disulfide is the first reported soil fumigant, used in Europe during the 1870's to control the sugar beet nematode. This agent is commercially impractical, however, since very large quantities must be applied (due to the high volatility) and the material is quite flammable, reportedly being ignited even by static electricity resulting from pouring the material out of drums. In addition, carbon disulfide possesses a very objectional odor, and its vapors are toxic to humans. When sold for fumigant use, the carbon disulfide is normally mixed with an inert fire retarding compound, such as carbon tetrachloride, and occasionally also with another fumigant. Typically, these compositions do not contain over about 20 percent by weight of carbon disulfide.

In addition to soil uses, carbon disulfide has been proven effective in the fumigation of commodities, as an insecticide, as a rodenticide, and for controlling certain weeds. W. T. Thomson, *Agricultural Chemicals - Book III Miscellaneous Chemicals*, 1976–77 Revision (Thomson Publications, P. O. Box 7964, Fresno, Calif.), describes application methods to grain entering storage and to stored grains, and the chamber fumigation of commodities, at pages 11–12. Examples are also given of methods for controlling apple tree borers and soil living rodents.

Carbon disulfide is approved by the U.S. Environmental Protection Agency as an insecticide, when used as a fumigant after harvest for barley, corn, oats, popcorn, rice, rye, sorghum (milo), and wheat.

Numerous compositions possessing nematocidal properties have been developed, including active ingredients such as the polyamines of U.S. Pat. No. 2,979,434 to Santmyer, the heterocyclic compounds of U.S. Pat. No. 2,086,907 to Hessel, and various halogenated compounds. Among the useful halogen-containing nematocides are 1,2-dibromoethane, methyl bromide, 3-bromopropyne, 1,2-dichloropropane, ethylene dichloride and others, all of which are quite phytotoxic, therefore restricting their utility to mostly preplanting treatments.

One compound which enjoyed considerable commercial success is 1,2-dibromo-3-chloropropane (DBCP), which can be used to control nematodes in soils with growing perennial plants. However, use of this material has been suspended due to a finding of undesirable reproductive system effects in workers exposed to the chemical, and the possibility that the compound is a carcinogen. The unavailability of DBCP has been a serious setback to growers of perennial crops, such as grapes, stone fruits and nuts, since these crops experience more severe cumulative nematode population increases, and most replacement soil fumigants are phytotoxic. U.S. Patents concerned with the use of DBCP as a soil fumigant include No. 2,937,936 to Schmidt and No. 3,049,472 to Swezey.

A further class of materials which have been utilized to control nematodes is the thiocarbonates. U.S. Pat. No. 2,676,129 to Bashour describes the preparation of lower aliphatic disubstituted trithiocarbonates having the structure as in (1):

(1)

wherein $R_1$ and $R_2$ are alkyl radicals having from three to nine carbon atoms. The compounds were dissolved in acetone and added to nematode-infested soils, resulting in control of the nematodes.

Other compounds have been reported by Seifter in U.S. Pat. Nos. 2,836,532 and 2,836,533, the former relating to the use of sodium trithiocarbonate, and the latter pertaining to alkali metal and ammonium salts of tetrathioperoxycarbonic acid. Both are described as effective in nematode control.

Another serious problem in agriculture is that of low nigrogen use-efficiency, since crops have been found to recover only 30 to 70 percent of the total amount of expensive fertilizer nitrogen which is applied to the soil. Most of the lost nitrogen is due to nitrite and nitrate ions, which are exceptionally mobile in a soil environment, and therefore are readily lost by surface runoff and also by leaching from the plant root zone into deeper soil. Other losses of these ions are due to denitrification, which is reduction to elemental nitrogen or gaseous nitrogen oxides under conditions of limited aeration. In addition to the direct economic losses, these nitrogen forms constitute environmental pollutants when runoff enters surface and ground water systems.

Although some nitrogen is applied to soil in the form of nitrate (e.g., ammonium nitrate-containing fertilizers), most nitrogen fertilization is with ammonia, ammonium compounds other than nitrate, and urea materials. Ammonium nitrogen is fairly tightly bound by various physical and chemical processes in a soil environment and, therefore, is much less subject to losses. Unfortunately, the bound ammonium nitrogen is also less available to plants.

The process of nitrification results in conversion of ammonium ions into nitrate ions. Microbial species known as nitrosomonas oxidize ammonium to nitrite; nitrobacter species oxidize nitrite to nitrate. This more mobile ion is easily taken up by plant roots and is also readily assimilated by plants. In this regard, the nitrification process is desirable, but control of the rate at which conversion occurs has not been easily obtained. Inhibition of the nitrification would tend to make the applied nitrogen available to plants over a longer period of time, resulting in an increased plant uptake efficiency.

Various compositions have been offered as inhibitors of nitrification, including expensive organic materials such as 2-chloro-6-(trichloromethyl)-pyridine, 2-amino-4-chloro-6-methyl-pyrimidine, sulfathiazole, alkanolysulfathiazoles, and others. A paper by J. M. Bremner and L. G. Bundy in Soil Biology and Biochemistry, Vol. 6, pages 161–165 (1974) describes the efficacy of various volatile organic sulfur compounds, including methyl mercaptan, dimethyl sulfide, dimethyl disulfide, cabon disulfide, and hydrogen sulfide; carbon disulfide in very small amounts is described as having "a remarkable inhibitory effect on nitrification of ammonium in soils incubated in closed systems". Carbon disulfide was tested in the field by J. Ashworth et al., Chemistry and Industry, Sept. 6, 1975, pages 749–750, and found to be effective as a nitrification inhibitor. Hawkins, in U.S. Pat. No. 4,078,912, describes the use of sodium, potassium and ammonium trithiocarbonates, and of xanthates, either alone or in fertilizer mixtures, to inhibit nitrification; the mode of operation is attributed to a release of carbon disulfide by the compounds.

One additional potential problem, which could be presented to the agricultural industry in the very near future, is the loss of the widely used, effective fumigant 1,2-dibromoethane, due to environmental concerns. This agent is approved for use on the same crops as is carbon disulfide, and is additionally used extensively in chambers for fumigating fruits and vegetables to control various insects.

The chemistry of thiocarbonic acids and salts has been studied in some detail, as indicated in the papers by O'Donoghue and Kahan, Journal of the Chemical Society, Vol. 89 (II), pages 1812–1818 (1906); Yeoman, Journal of the Chemical Society, Vol. 119, pages 38–54 (1921); and Mills and Robinson, Journal of the Chemical Society, Vol. 1928 (II), pages 2326-2332 (1928). According to O'Donoghue and Kahan, derivatives of thiocarbonic acid were prepared by Berzelius, who reacted aqueous solutions of hydrosulfides with carbon disulfide, the reactions occurring as in (2):

$$2KHS + CS_2 \rightarrow K_2CS_3 + H_2S \qquad (2)$$

giving unstable solutions which yielded unstable crystalline salts.

Pure thiocarbonates were prepared and further characterized by O'Donoghue and Kahan. Their paper, at page 1818, reports the formation of ammonium thiocarbonate by reacting liquid ammonia with cold alcoholic thiocarbonic acid, prepared by dropping a solution of calcium thiocarbonate into concentrated hydrochloric acid, and postulates the decomposition of the compound as proceeding according to (3) and (4):

$$(NH_4)_2CS_3 \rightarrow (NH_4)_2S + CS_2 \qquad (3)$$

$$(NH_4)_2CS_3 \rightarrow 2NH_3 + H_2S + CS_2 \qquad (4)$$
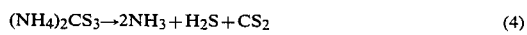

The noted paper by Yeoman, which is incorporated herein by reference, reports the further study of thiocarbonates (called trithiocarbonates therein) and also reports the preparation and properties of perthiocarbonates (or tetrathiocarbonates), derivatives of tetrathiocarbonic acid, $H_2CH_4$. Yeoman prepared ammonium trithiocarbonate by saturating an alcoholic ammonia solution with hydrogen sulfide, and then adding carbon disulfide; dry ether was added to precipitate the product salt. Ammonium perthiocarbonate was prepared in a similar manner, except that after reacting the ammonia and hydrogen sulfide, elemental sulfur was added to form the disulfide, $(NH_4)_2S_2$; adding carbon disulfide immediately precipitated the product.

Yeoman states that "solutions of both ammonium trithiocarbonate and perthiocarbonate are very unstable" (page 52), due to both decomposition to form thiocyanate as a product, and to "complete dissociation into ammonia, hydrogen sulfide, and carbon disulfide."

Considerable explanation is provided concerning the stability of thiocarbonates, as exemplified by sodium trithiocarbonate and perthiocarbonate. Sodium trithiocarbonate solutions in water are said to remain stable only if oxygen and carbon dioxide are "rigidly excluded"; the presence of oxygen causes decomposition to form carbon disulfide and thiosulfates, while carbon dioxide decomposes the solution to give a carbonate and carbon disulfide. Similarly, solutions of sodium perthiocarbonate are reported to be stable for a considerable time in the absence of oxygen, the presence of air causing decomposition into thiosulfate and carbon disulfide, while carbon dioxide decomposes the compound to form a carbonate, elemental sulfur, carbon disulfide, and hydrogen sulfide.

The previously noted paper by Mills and Robinson shows the preparation of ammonium thiocarbonate by digesting ammonium pentasulfide (obtained by suspending sulfur in aqueous ammonia, then saturating with hydrogen sulfide) with carbon disulfide. A crystalline residue from this digestion was found to be ammonium perthiocarbonate. These authors prepared a "better" ammonium perthiocarbonate product, however, by extracting the ammonium pentasulfide with carbon disulfide in a Soxhlet apparatus.

A need exists for a fluid which can release carbon disulfide for fumigation and nitrification inhibiting purposes, but which can be stored and handled safely and without significant loss of effectiveness during a reasonable commercial storage and delivery cycle.

It is therefore an object of the present invention to provide a stabilized liquid composition which can be caused to release fumigants, including carbon disulfide.

It is a further object to provide a stabilized composition which is miscible with water to form a fumigant and nitrification inhibitor which can be applied to soils by means of fluid handling equipment or introduced into irrigation water.

Another object is to provide a stabilized fumigant and nitrification inhibitor which can be mixed and applied together with liquid fertilizers.

These, and other objects, will more clearly appear from consideration of the following disclosure.

SUMMARY OF THE INVENTION

The stabilized fumigant composition of this invention comprises an aqueous solution usually containing up to about fifty percent by weight of a solute comprising ammonia, hydrogen sulfide, and carbon disulfide, wherein the molarity of hydrogen sulfide is greater than the molarity of carbon disulfide, and is about one-half the molarity of ammonia. Sulfur can also be present in the solute.

This composition is stable during prolonged periods of storage in a closed container, exhibits a low vapor pressure, and is not flammable. The composition is miscible with water and decomposes to form its original components. A fertilizer material, such as ammonia and/or urea, can be added to the composition to enhance its plant nutrient content and permit a simultaneous field application.

DESCRIPTION OF THE INVENTION

In accordance with the invention, there are provided stabilized compositions which are effective as both fumigants and nitrification inhibitors.

The term "stability", as used herein, can be regarded as a composite of two concepts: chemical stability and physical stability. Since the effectiveness of a composition depends, at least in part, upon its ability to release carbon disulfide during decomposition, chemical stability is expressed accordingly; this can be quantified by, for example, chemically decomposing the composition at some time and measuring the amount of carbon disulfide which evolves. Alternatively, an indication of the amount of available carbon disulfide can be obtained by spectrophotometrically determining the presence of the thiocarbonyl bond ($>C=S$) in a sample of the composition. The absorbance at wavelengths corresponding to those at which thiocarbonyl is known to absorb energy can be used for a quantitative analysis.

Symptomatic of chemical stability, but having an independent significance, is physical stability. This concept is important due to the nature of the products formed during decomposition of the composition, particularly the ammonia, hydrogen sulfide, and carbon disulfide, which each have a high vapor pressure. It is readily apparent that a change in the physical form of the composition from a solution of low vapor pressure into a mixture of compounds, each possessing a high vapor pressure, imposes some rather stringent requirements upon storage containers. Vapor pressure above the composition of the invention, therefore, will be used herein as an indicator of physical stability; a condition of maintained low vapor pressure is the desired property. Another index of physical instability is the formation of undesirable insoluble precipitates, which frequently comprise sulfur, or of an immiscible liquid phase, such as carbon disulfide. The more general description of physical stability, then, is the maintenance of only a single phase in the composition.

Assessment of the stability of a particular composition must involve consideration of both the chemical stability and the physical stability over a period of time during which stability is desired. Certain formulations do not form precipitates and do not develop high vapor pressures during a reasonable storage period, and therefore may be preferred over a formulation which has a greater chemical stability, but develops objectionable physical characteristics during storage. As a further example, a composition which is intended to be used as an additive to irrigation water is likely to be selected for its freedom from precipitate formation upon dilution; to obtain this property, a composition having a lower chemical stability could be necessary.

The compositions of this invention are normally prepared by mixing the components (ammonia, hydrogen sulfide, carbon disulfide, water, and, optionally, sulfur) in the proper proportions, and under conditions which facilitate removal of the heat generated during the preparation. Most of this heat results from the mixing of ammonia and hydrogen sulfide, and from the addition of carbon disulfide to the other components. No particular order of component addition is required, except that ammonia must either be present prior to hydrogen sulfide addition or must be added concurrently with the hydrogen sulfide. In a typical batch preparation, the required amount of water will be introduced into a container (which has cooling coils or other heat exchanging means), followed by the sequential additions of gaseous or liquid ammonia and hydrogen sulfide, sulfur (if required), and carbon disulfide.

Many variations in the foregoing preparation are possible. For example, ammonia can be added as an aqueous ammonia solution, to satisfy all, or some part, of the ammonia requirement, reducing the amount of cooling needed. A further reduction in cooling can be obtained by using an ammonium sulfide solution or solid to provide any desired amount of the ammonia and hydrogen sulfide requirement. Sulfur, if required, can be added as the element or as a solution in carbon disulfide.

It is possible to replace a portion of the ammonia and hydrogen sulfide with a soluble sulfide material such as alkali metal sulfide, alkaline earth metal sulfide, or any mixture thereof. The maximum replaced portion will usually be equivalent in sulfide content to that amount of hydrogen sulfide which would exceed the carbon disulfide molarity in a particular composition. These alternative compositions are especially useful for soil treatment, when it is desired to incorporate plant nutrients not otherwise present, e.g., potassium and magnesium, for correcting a soil deficiency.

A typical continuous-flow production of the composition includes dissolving molten sulfur in carbon disulfide, using a mixing vessel which can be cooled, for example, by external recycle through a heat exchanger, followed by combining the sulfur solution with water, liquid ammonia and liquid hydrogen sulfide in a cooled reactor vessel.

The reactor in either a batch or continuous process should be maintained at a somewhat elevated temperature, e.g., about 75° F. to about 150° F., to promote the rapid formation of a clear solution. Stirring or other mixing of the reactor contents also is useful in this regard. A holding time of about one hour is normally sufficient for obtaining the desired product solution.

A stabilized fumigant and nitrification inhibitor which is obtained by the above preparations comprises an aqueous solution of up to about fifty percent by weight solute, in which solute the molarity of hydrogen sulfide is greater than the molarity of carbon disulfide, and is about one-half the molarity of ammonia, and in which sulfur can also be present. Were it not for the requirement that the hydrogen sulfide molarity exceeds that of the carbon disulfide, the range of solute compositions could include the stoichiometric equivalents of ammonium trithiocarbonate and ammonium tetrathiocarbonate. This requirement, in fact, is an important factor in obtaining the enhanced stability exhibited by the compositions of this invention.

One theoretical basis for explaining the enhancement in stability which is obtained by means of the invention can be inferred from the following equations, although we do not intend to be bound by any one particular theory, since other possible explanations could be developed. In the equations, likely equilibrium conditions are indicated by the double arrows, while reactions which are considered to be primarily irreversible are denoted by a single arrow. Equilibration between ammonium tetrathiocarbonate and ammonium trithiocarbonate is shown in (5); equilibrium between ammonium trithiocarbonate and its components is represented by (6); a possible decomposition route of ammonium trithiocarbonate into ammonium dithiocarbamate is in (7); equilibrium of ammonium dithiocarbamate with ammonia and carbon disulfide in an acidic environment is shown by (8); the decomposition of ammonium dithiocarbamate into ammonium thiocyanate is represented by (9).

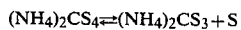
$(NH_4)_2CS_4 \rightleftharpoons (NH_4)_2CS_3 + S$ (5)

$(NH_4)_2CS_3 \rightleftharpoons 2NH_3 + H_2S + CS_2$ (6)

$(NH_4)_2CS_3 \rightarrow NH_2CS_2NH_4 + H_2S$ (7)

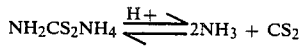
$NH_2CS_2NH_4 \xrightleftharpoons{H+} 2NH_3 + CS_2$ (8)

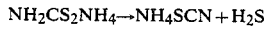
$NH_2CS_2NH_4 \rightarrow NH_4SCN + H_2S$ (9)

From (5), a prediction can be made that increased stability will result from an excess of elemental sulfur in the composition. This effect has been confirmed.

Using the expression of (6), it can be inferred that an excess of a component will shift the equilibrium to favor maintenance of ammonium trithiocarbonate. This has been disproved in the case of excess carbon disulfide, and also for excess ammonia. The effect of ammonia, however, appears to be expressible as a quadratic function, destabilizing solutions of ammonium trithiocarbonate as the excess ammonia increases, then reversing to provide increasing stability with continued increases in the ammonia level. For excess hydrogen sulfide, however, a stabilizing effect has been found, expressible as a quadratic function to reflect the stabilization as hydrogen sulfide concentration is increased to a particular level, then a decrease in stability for higher levels of hydrogen sulfide.

The reactions of (7) and (9) show a mechanism for the decomposition which results in forming ammonium thiocyanate, thereby destroying the thiocarbonyl bond and preventing the release of carbon disulfide by the composition. According to (8), however, acidic conditions can cause the intermediate product to release carbon disulfide.

Some general parameters which have been determined to affect composition physical stability are as follows for a composition which is an aqueous solution of about 45 percent by weight of a solute comprising hydrogen sulfide, ammonia (at twice the molarity of hydrogen sulfide), carbon disulfide, and sulfur:

(a) the composition is stable for several months without hydrogen sulfide evolution if (1) sulfur molarity is greater than or equal to carbon disulfide molarity, and (2) hydrogen sulfide molarity is less than 1.5 times the carbon disulfide molarity;

(b) for the case described above in (a), carbon disulfide will separate into a separate phase if its molarity is greater than that of hydrogen sulfide; and (c) the composition is stable for several months without sulfur precipitation if (1) sulfur molarity is less than or equal to carbon disulfide molarity, and (2) hydrogen sulfide molarity equals carbon disulfide molarity.

The solubility limit of a composition is approximately 50 to 55 percent by weight solute, showing some variability which is dependent upon relative amounts of the various components present. Release of carbon disulfide is rapidly accelerated upon dilution of the composition with water. Some of the possible compositions of the invention, however, are not suitable for uses which require dilution, because of the resulting sulfur precipitation. In general, sulfur precipitation occurs within a few days if (1) hydrogen sulfide molarity (present with approximately twice its molarity of ammonia) is less than about 1.5 times the molarity of carbon disulfide, (2) sulfur molarity is greater than carbon disulfide molarity, and (3) carbon disulfide is less than about 2.5 percent by weight in the composition.

As a practical matter, the least tolerable manifestation of physical instability is gas evolution, since this causes stresses on the storage container which could result in releasing toxic and flammable or explosive vapors.

The compositions of this invention are stabilized against significant increases in vapor pressure, and against significant solid or immiscible liquid phase formation, during reasonable storage periods, and also maintain acceptable chemical stability during such periods.

Soil application of a composition can be accomplished either prior to planting or after plant growth is established. It should be noted, however, that different plant species exhibit differing tolerances to chemical agents. In addition, phytotoxicity to a particular plant can be dependent upon its growth stage. Germination is not inhibited for most plant seeds after soil treatment, and growth of established plants is not significantly altered. Some seedlings, though, show phytotoxicity symptoms. Postplant applications of the composition to such diverse crops as corn, cotton, tomatoes, potatoes and grapes have given no indications of phytotoxicity at effective nematocidal application rates, but cucumber plants have been shown to be somewhat sensitive to the composition.

The composition can be applied in its undiluted form (to minimize the amount which is required per acre) by spraying onto the soil surface, preferably followed within several hours by water application to move the composition into the soil before a significant amount of free carbon disulfide is released. Injection into the soil, using a shank or knife, is also a useful method for applying the composition. This application can either be "flat", wherein the injectors are closely spaced to treat essentially the entire field area, or can be "localized" by spacing the injectors such that only the plant growing bed is treated, in bands.

Alternatively, those forms of the composition which are physically stable upon dilution can be mixed into irrigation water and applied by any customary manner, such as through sprinklers, in the water for furrow or flood irrigation, and in drip irrigation systems. The composition will move into the soil with the water, and decompose to accomplish its fumigation and nitrification inhibition functions.

The compositions also can be used in non-soil fumigation procedures, such as in the chamber fumigation of commodities which are introduced into commerce. In this type of procedure, dilution of a composition or the application of heat, or both, can be used to promote a rapid decomposition into the fumigant components. Upon termination of the fumigation procedure, vapors in the chamber can be drawn through a scrubbing system, e.g., one containing an alkaline aqueous solution, to remove the fumigant and prevent atmospheric pollution when the chamber is opened.

Another important use of the compositions is as a fumigant for stored grains and other agricultural products. If applied to products which are to be stored, a composition can be applied simply by spraying into the product as it is being transported to the storage enclosure with a conveyor, auger or other device. A composition can also be applied to agricultural products which are already in storage, by spraying onto the exposed products and sealing the storage enclosure.

It is also possible to use the compositions for fumigating rooms or storage enclosures; this is accomplished by spraying the floor and walls with composition, and sealing the space until the desired fumigation is accomplished. As an alternative to spraying, a technique similar to chamber fumigation can be used, wherein heat decomposes the composition in an enclosed space.

The fumigating ability of compositions described herein has been expressed primarily in terms of the available carbon disulfide content. It should be noted, however, that other components can contribute to efficacy as a fumigant. Ammonia, for example, is a registered fungicide for use on harvested grapefruit, lemons, oranges, and on grain for feed use. In addition, sulfur is very widely used as a fungicide-acaricide-insecticide, so any of the compositions of the invention which decompose to form sulfur will have similar properties in addition to the properties attributable to the carbon disulfide content.

Upon dilution, heating or introduction into the soil (which can be considered as a form of dilution), the compositions of the invention break down into their components by a process which can be conceptualized as a physical dissociation. In a soil environment, the ammonia and hydrogen sulfide components are rapidly withdrawn into soil particles, and thereby rendered more or less immobile, depending upon soil characteristics, moisture, ambient temperature and the like. Carbon disulfide, however, is not tightly bound to the soil and readily migrates to perform the fumigation function.

The invention is further illustrated by the following examples which are illustrative of various aspects of the invention, and are not intended as limiting the scope of the invention as defined by the appended claims.

EXAMPLE 1

Preparation of a composition of the invention is accomplished, using a 12 liter, three-neck, round-bottom flask, fitted with a sealed stirrer, gas delivery tube, and a U-tube manometer. A 5461 gram charge of water is placed in the flask, and 1266 grams of anhydrous ammonia are added with cooling of the flask and stirring. With further cooling, 1266 grams of hydrogen sulfide are added. To the resulting solution are added 595 grams of finely divided sulfur and, with resumed cooling, 1412 grams of carbon disulfide are also added. Stirring is continued while the mixture is maintained at a temperature between about 75° F. and about 100° F. for a period of about one hour. The resulting clear, deep yellow solution has a composition as follows:

| Component | Weight Percent | Mole Percent |
|---|---|---|
| $NH_3$ | 12.66 | 16.46 |
| $H_2S$ | 12.66 | 8.22 |
| S | 5.95 | 4.11 |
| $CS_2$ | 14.12 | 4.11 |
| $H_2O$ | 54.61 | 67.1 |

This solution has a specific gravity at 70° F. of 1.130, and a crystallization temperature of about 14° F.

EXAMPLE 2

Solutions corresponding in stoichiometry to an ammoniated ammonium trithiocarbonate are prepared by the procedure of Example 1. The chemical stability is determined by measuring absorbance at wavelengths corresponding to those of the thiocarbonyl group (10.0 microns) and the thiocyanate group (4.85 microns) at the time of preparation and at subsequent times, using Fourier-transform infrared spectrophotometry.

When the infrared data are expressed as the result of thiocarbonyl absorbance divided by the sum of thiocarbonyl absorbance plus thiocyanate absorbance (called "absorbance ratio" in this and subsequent examples), a plot can be made versus elapsed time since composition preparation. The natural logarithm of the absorbance ratio is a linear function of elapsed time, so a linear regression by the method of least squares is used to calculate the equation of this line. By solving the equation for an absorbance ratio of one-half of its original value, the "half-life" of the composition is calculated.

Results are obtained as follows:

| Composition, mole percent | | | | Absorbance Ratio | Half-Life, |
|---|---|---|---|---|---|
| $NH_3$ | $H_2S$ | $CS_2$ | $H_2O$ | 0, 2, 4.7 Months | Months |
| 9.93 | 4.14 | 4.13 | 81.80 | 1, 0.45, 0.18 | 2.0 |
| 11.57 | 4.13 | 4.13 | 80.16 | 1, 0.42, 0.16 | 1.9 |
| 13.23 | 4.13 | 4.13 | 78.51 | 1, 0.44, 0.19 | 2.2 |

EXAMPLE 3

The experiment of Example 2 is repeated with solutions containing sulfur, and varying amounts of other components, yielding compositions as tabulated:

| Formula Number | Composition, Mole Percent | | | | |
|---|---|---|---|---|---|
| | $NH_3$ | $H_2S$ | $CS_2$ | S | $H_2O$ |
| 1 | 9.38 | 4.69 | 4.70 | 4.70 | 76.53 |
| 2 | 13.06 | 6.53 | 4.76 | 4.77 | 70.88 |
| 3 | 13.32 | 6.66 | 4.86 | 7.42 | 67.74 |
| 4 | 14.52 | 7.26 | 4.79 | 4.79 | 68.64 |
| 5 | 16.47 | 8.23 | 4.11 | 4.11 | 67.07 |
| 6 | 16.80 | 8.40 | 4.18 | 6.73 | 63.89 |

It should be noted that Formula 1 corresponds stoichiometrically to a solution of ammonium tetrathiocarbonate.

Infrared absorption determinations are made using these compositions giving the following calculated half-lives:

| Formula Number | Absorbance Ratio | | | | Half-life, |
|---|---|---|---|---|---|
| | 0 Months | 5.5 Months | 12 Months | 15 Months | Months |
| 1 | 0.95 | 0.63 | 0.62 | 0.37 | 11.9 |
| 2 | 0.96 | 0.74 | 0.66 | 0.53 | 17.7 |
| 3 | 0.96 | 0.80 | 0.72 | 0.62 | 25.8 |
| 4 | 0.96 | 0.78 | 0.67 | 0.37 | 13.1 |
| 5 | 0.96 | 0.67 | 0.58 | 0.48 | 14.2 |
| 6 | 0.95 | 0.70 | 0.60 | 0.48 | 14.8 |

These data show that increasing the content of soluble sulfide enhances chemical stability, and that a further enhancement can be obtained by increasing the sulfur content.

EXAMPLE 4

The compositions of Example 3 are evaluated for physical stability by placing the prepared solutions in a closed container and measuring absolute vapor pressure by flashing the liquid into an evacuated chamber which is connected to an open-tube manometer. The following measurements are obtained:

| Formula Number | Absolute Vapor Pressure, mm. Hg | |
|---|---|---|
| | 0 Months | 6 Months |
| 1 | 222 | — |
| 2 | 93 | — |
| 3 | 154 | — |
| 4 | 99 | — |
| 5 | 112 | 274 |
| 6 | 204 | 224 |

All of the formulae have an acceptable vapor pressure at the time of formulation, but the first four formulae each become strongly effervescent during storage, rendering the subsequent vapor pressure measurements unreliable. In addition, an unidentified solid is formed in the container with Formula 1, prior to the six month measurement.

These data demonstrate the enhancement in physical stability which is attributable to an excess of soluble sulfide in the composition.

EXAMPLE 5

Using the procedure of Example 2, chemical stability (in terms of solution half-life) is determined over a period of six months for various compositions prepared according to the method of Example 1. In addition, absolute vapor pressure over the liquid in a closed container is measured at the time of preparing the composition.

Results are as tabulated:

| Composition, Mole Percent | | | | | Half-life, | Absolute Vapor |
|---|---|---|---|---|---|---|
| $NH_3$ | $H_2S$ | $CS_2$ | S | $H_2O$ | Months | Pressure, mm. Hg |
| 9.74 | 4.87 | 4.64 | 4.64 | 76.11 | 13.0 | 254 |
| 11.66 | 4.87 | 4.64 | 4.64 | 74.20 | 9.1 | 102 |
| 13.60 | 4.86 | 4.63 | 4.63 | 72.28 | 7.6 | 81 |
| 15.52 | 4.86 | 4.62 | 4.62 | 70.38 | 6.6 | 80 |
| 10.70 | 5.34 | 4.65 | 4.65 | 74.65 | 11.9 | 209 |
| 12.81 | 5.34 | 4.65 | 4.65 | 72.56 | 10.9 | 83 |
| 14.94 | 5.34 | 4.65 | 4.65 | 70.44 | 7.6 | 80 |
| 17.05 | 5.34 | 4.65 | 4.65 | 68.35 | 7.2 | 87 |
| 10.77 | 5.38 | 4.68 | 5.62 | 73.54 | 17.2 | 323 |
| 12.91 | 5.38 | 4.68 | 5.62 | 71.41 | 11.8 | 92 |
| 15.04 | 5.38 | 4.68 | 5.62 | 69.31 | 7.8 | 73 |
| 17.19 | 5.38 | 4.68 | 5.62 | 67.17 | 7.0 | 90 |
| 10.85 | 5.43 | 4.72 | 6.61 | 72.34 | 17.7 | — |
| 13.00 | 5.43 | 4.72 | 6.61 | 70.27 | 11.7 | 107 |
| 15.16 | 5.43 | 4.72 | 6.61 | 68.12 | 8.1 | 79 |
| 17.30 | 5.43 | 4.72 | 6.61 | 66.01 | 7.0 | 77 |
| 9.92 | 4.96 | 3.97 | 3.96 | 77.19 | 15.2 | 158 |
| 11.89 | 4.96 | 3.97 | 3.96 | 75.22 | 10.9 | 83 |
| 13.87 | 4.96 | 3.97 | 3.96 | 73.26 | 7.9 | 77 |
| 15.81 | 4.96 | 3.97 | 3.96 | 71.33 | 7.4 | 80 |
| 9.98 | 4.99 | 3.99 | 4.79 | 76.24 | 18.0 | 203 |
| 11.97 | 4.99 | 3.99 | 4.79 | 74.27 | 11.3 | 81 |
| 13.96 | 4.99 | 3.99 | 4.79 | 72.29 | 7.9 | 71 |
| 15.92 | 4.99 | 3.99 | 4.79 | 70.36 | 7.4 | 81 |
| 10.05 | 5.03 | 4.02 | 5.63 | 75.28 | 15.3 | 226 |
| 12.04 | 5.03 | 4.02 | 5.63 | 73.30 | 10.5 | 78 |
| 14.04 | 5.03 | 4.02 | 5.63 | 71.34 | 7.7 | 70 |
| 16.02 | 5.03 | 4.02 | 5.63 | 69.38 | 7.4 | 80 |
| 14.32 | 7.16 | 4.72 | 4.72 | 69.08 | 19.4 | 118 |
| 18.56 | 7.14 | 4.70 | 4.70 | 64.89 | 12.8 | 106 |
| 22.79 | 7.13 | 4.69 | 4.70 | 60.69 | 10.8 | 140 |
| 14.54 | 7.27 | 4.79 | 6.70 | 66.70 | 20.7 | 129 |
| 18.84 | 7.25 | 4.77 | 6.68 | 62.46 | 13.3 | 101 |
| 23.13 | 7.23 | 4.76 | 6.67 | 58.20 | 10.9 | 135 |
| 14.64 | 7.32 | 4.82 | 7.71 | 65.51 | 20.7 | 129 |
| 18.99 | 7.31 | 4.81 | 7.70 | 61.19 | 13.3 | 96 |
| 23.29 | 7.28 | 4.80 | 7.67 | 56.95 | 10.8 | 133 |
| 19.20 | 9.60 | 4.80 | 4.80 | 61.59 | 14.6 | 152 |
| 24.89 | 9.57 | 4.79 | 4.79 | 55.96 | 12.8 | 168 |
| 19.47 | 9.73 | 4.87 | 6.82 | 59.11 | 14.6 | 145 |
| 25.24 | 9.70 | 4.85 | 6.79 | 53.41 | 12.8 | 166 |
| 19.63 | 9.82 | 4.91 | 7.86 | 57.79 | 16.9 | 150 |
| 25.44 | 9.78 | 4.89 | 7.83 | 52.04 | 13.9 | 168 |

Using a multiple linear regression technique, an equation is derived from the data of this example, which can be used to predict the chemical stability of a composition. The equation (10) is as follows, wherein t is the solution half-life (in months) and X is the mole percentage of its subscripted component:

$$t = -34.5 - 2.7X_{NH_3} + 0.053X_{NH_3}^2 + 16.8X_{H_2S} - 0.092X_{H_2S}^2 - 2.0X_{CS_2} + 0.65X_S + 0.21X_{H_2O} \qquad (10)$$

The data are found to fit this equation quite well, as indicated by the regression correlation of 0.95.

A similar regression calculation is performed, using the vapor pressure data, to predict this physical property of a composition. In the following equation (11), ln(VP) is the natural logarithm of the absolute vapor pressure (millimeters mercury) and X is again mole percentage of the subscripted component.

$$\ln(VP) = 1.907 - 0.447 X_{NH_3} + 0.013 X_{NH_3}^2 + 0.578 X_{H_2S} - 0.027 X_{H_2S}^2 + 0.258 X_{CS_2} + 0.0248 X_S + 0.040 X_{H_2O} \quad (11)$$

The fit of data is measured by the correlation of 0.86 which is obtained.

EXAMPLE 6

The rate at which carbon disulfide is lost from diluted compositions of this invention is determined by bubbling nitrogen through the solutions, and measuring the carbon disulfide content of the gas which leaves the solution, using a mass spectrometer.

In the determination, the solution, corresponding to that of Example 1 (containing 14.1 percent by weight carbon disulfide), is compared to pure carbon disulfide, and to serial dilutions of the Example 1 solution with water, which prepared 10, 1 and 0.1 volume percent solutions of the original composition.

Results are as tabulated, wherein k is the calculated first order rate constant for loss of carbon disulfide, and t is the solution half-life.

| Composition | $k \left( \dfrac{1}{\text{hour}} \right)$ | t (hours) |
|---|---|---|
| CS$_2$ | 2.0 | — |
| Ex. 1, 100% | 0.003 | 230 |
| Ex. 1, 10% | 0.14 | 5.0 |
| Ex. 1, 1% | 1.09 | 0.6 |
| Ex. 1, 0.1% | 1.35 | 0.5 |

It should be noted that the value of k for the 0.1 percent solution is approximately 70 percent of the value obtained for pure carbon disulfide.

EXAMPLE 7

The utility as nematocides for compositions of this invention is demonstrated in a greenhouse experiment with tomato plants.

In the experiment, eighty containers are used, each containing about 500 grams of sterilized sandy loam soil. Each container is given four 5-milliliter injections of extract from nematode-infested pepper roots, one inch below the soil surface, producing an initial population of 2000 root-knot nematode larvae (species *Meloidogyne incongnita*) per container.

Twenty treatments are replicated four times, each treatment consisting of solution injection into the soil at a two inch depth. The treatments include each of the six compositions from Example 3 at three levels, plus one level of the known nematocide 1,2-dibromo-3-chloropropane (DBCP), and a control with only water injected. After injection, each container is enclosed in a plastic bag and placed in the shade for three days. Upon removing the bags, the soils are aerated by stirring, and allowed to stand undisturbed for eight additional days. Following an additional aeration, a tomato seedling is planted in each pot.

Each container receives 25 milligrams nitrogen (as calcium nitrate) immediately after planting, followed by 2 grams of Osmocote, a slow release complete fertilizer.

The plants are harvested after 37 days of growth, and soil is removed from the roots by a gentle washing with water. By use of a magnifying glass, the number of root galls is counted on each plant. Roots and tops are then separated by cutting, oven dried at 80° C. and weighed.

Results are as shown in the table, in which the "Application" represents milligrams of treatment per kilogram of soil, calculated as contained carbon disulfide for the Example 3 solutions. Gall counts and weights are mean values from the four replicates.

| Treatment Solution | Application, ppm | Gall Count | Dry Weight, Grams | |
|---|---|---|---|---|
| | | | Total | Roots |
| None | — | 24.3 | 1.338 | 0.335 |
| DBCP | 50 | 0* | 1.238 | 0.273 |
| 1 | 22 | 1.3* | 0.933 | 0.175 |
| 1 | 43 | 3.8 | 1.058 | 0.178 |
| 1 | 65 | 1.3* | 0.750 | 0.155 |
| 2 | 22 | 8.3 | 1.323 | 0.298 |
| 2 | 43 | 5.3 | 1.393 | 0.325 |
| 2 | 65 | 5.0 | 1.350 | 0.292 |
| 3 | 22 | 6.5 | 1.135 | 0.253 |
| 3 | 43 | 2.0* | 1.505 | 0.325 |
| 3 | 65 | 4.5 | 1.060 | 0.220 |
| 4 | 22 | 4.5 | 1.145 | 0.243 |
| 4 | 43 | 3.3* | 1.458 | 0.303 |
| 4 | 64 | 1.5* | 1.588 | 0.353 |
| 5 | 22 | 7.5 | 1.178 | 0.253 |
| 5 | 43 | 1.0* | 1.930 | 0.415 |
| 5 | 65 | 0.8* | 1.235 | 0.228 |
| 6 | 22 | 6.3 | 1.503 | 0.313 |
| 6 | 43 | 3.5* | 1.688 | 0.368 |
| 6 | 64 | 1.0* | 1.635 | 0.345 |

The gall counts marked by an asterisk are considered to be statistically indistinguishable.

All of the treatments are found to be effective against the nematodes; the degree of control which is provided, as measured by gall counts, apparently is directly dependent upon the application rate, expressed in terms of the carbon disulfide content.

No significant phytotoxicity is observed for the solution of this invention under conditions shown; strong evidence is seen that Solution 1 (corresponding stoichiometrically to ammonium tetrathiocarbonate) is somewhat phytotoxic at the application rates listed. Further, it should be noted that the stabilized compositions of the invention exhibit a trend toward accelerating tomato plant growth.

EXAMPLE 8

The nematocidal efficacy of the components of the invention is demonstrated by application to established grapevines.

In this test, Solutions 1, 2 and 3 from Example 3 are compared with 1,2-dibromo-3-chloropropane (as the commercial formulation Nemagon 12EC) on grapevines planted seven feet apart, in rows spaced at ten foot intervals. Single vines, replicated six times, are treated with nine soil injections spaced six inches apart in a single four-foot band centered on, and eight inches from, the vine trunk, paralleling the row. Only one side of the vine is treated.

Soil samples at two depths, 4 to 12 inches and 12 to 24 inches, are taken at locations six to eight inches outside the band, both immediately before, and 31 days after treatment. These samples are analyzed for the numbers of larvae of various nematode genera.

The Table shows results which are obtained. Application is shown as the number of gallons per acre, assuming that the vines would be treated equally on both sides of the row. The line for no treatment represents the injection of only water. All values are for the mean values obtained in the six replicates, calculated as nematode larvae per kilogram of soil.

| Treatment Solution | Application g.p.a. | Nematode Larvae Population, 31 Days | | | | | |
|---|---|---|---|---|---|---|---|
| | | Root-Knot | | Stubby Root | | Dagger | |
| | | 4-12" | 12-24" | 4-12" | 12-24" | 4-12" | 12-24" |
| None | — | 198 | 93 | 5 | 1 | 16 | 6 |
| Nemagon 12EC | 4.7 | 3 | 5 | 0 | 0 | 0 | 0 |
| 1 | 60 | 71 | 70 | 0 | 0 | 7 | 0 |
| 1 | 120 | 42 | 52 | 0 | 0 | 0 | 3 |
| 1 | 180 | 12 | 31 | 0 | 0 | 0 | 0 |
| 2 | 60 | 84 | 21 | 0 | 0 | 11 | 0 |
| 2 | 120 | 28 | 17 | 0 | 0 | 2 | 0 |
| 2 | 180 | 15 | 13 | 0 | 0 | 1 | 0 |
| 3 | 60 | 33 | 33 | 0 | 0 | 2 | 2 |
| 3 | 120 | 17 | 12 | 0 | 0 | 3 | 0 |
| 3 | 180 | 12 | 10 | 0 | 0 | 0 | 0 |

The pretreatment nematode counts per kilogram of soil are as follows: Root Knot (Meloidogyne spp.) 185 at 4-12 inches, 164 at 12-24 inches; Stubby Root (Trichodorus spp.) 4 at 4-12 inches, 6 at 12-24 inches; Dagger (Xiphinema spp.) 50 at 4-12 inches, 20 at 12-24 inches.

A clear correlation is noted between application rate and nematode population reduction. Also noteworthy is a comparison between Solution 1, corresponding stoichiometrically to ammonium tetrathiocarbonate, and the compositions of the invention, with regard to the effectiveness at greater soil depths. Since the invention results in stabilization against decomposition, a better movement of active ingredients through the soil can be obtained for a given application rate, through the practice of the invention.

EXAMPLE 9

The ability of compositions of this invention to combine with nitrogenous chemical fertilizers is demonstrated by dissolving urea in a solution corresponding to that prepared in Example 1, preparing solutions as tabulated:

| Percent Urea (Weight) | Crystallization Temp. (°F.) | Fertilizer Designation | Equivalent $CS_2$ (Wt. %) |
|---|---|---|---|
| 0 | 14 | 10.4-0-0-29.7(S) | 14.1 |
| 10 | −8 | 14.0-0-0-26.8(S) | 12.7 |
| 20 | −33 | 17.6-0-0-21.4(S) | 11.3 |
| 30 | −12 | 21.3-0-0-20.8(S) | 9.9 |
| 40 | 30 | 24.9-0-0-17.8(S) | 8.5 |
| 50 | 79 | 28.5-0-0-13.9(S) | 7.1 |

A minimum crystallization temperature is found at about 20 percent by weight urea, corresponding approximately to a urea-carbon disulfide mole ratio of 2:1. These solutions have stabilities similar to that of ammonium tetrathiocarbonate solutions, developing slight pressures of hydrogen sulfide over a period of several weeks.

The solutions are useful as providing a means for single application of nitrogen fertilization combined with fumigation and nitrification inhibition.

Various embodiments and modifications of this invention have been described in the foregoing examples and description, and further modification will be apparent to those skilled in the art. Such modifications are included within the scope of the invention as defined by the following claims.

We claim:

1. A method for inhibiting nitrification in soil, which comprises applying to the soil a composition comprising an aqueous solution containing a solute which comprises ammonia, hydrogen sulfide, and carbon disulfide, wherein the molarity of hydrogen sulfide is greater than the molarity of carbon disulfide, and is about one-half the molarity of ammonia.

2. The method defined in claim 1, wherein said solute further includes sulfur, in an amount up to about twice the molarity of carbon disulfide.

3. The method defined in claim 2, wherein carbon disulfide comprises up to about 20 percent by weight.

4. The method defined in claim 2, wherein the molarity of sulfur is equal to or greater than the molarity of carbon disulfide.

5. The method defined in claim 4, wherein the molarity of hydrogen sulfide is up to about 2 times the molarity of carbon disulfide.

6. The method defined in claim 5, wherein the molarity of sulfur is greater than the molarity of carbon disulfide.

7. The method defined in claim 6, wherein the molarity of hydrogen sulfide is about 1.5 times the molarity of carbon disulfide, and the molarity of sulfur is about 1.6 times the molarity of carbon disulfide.

8. The method defined in claim 1, wherein carbon disulfide comprises up to about 25 percent by weight.

9. The method defined in claim 1, wherein said composition is applied as a mixture with a nitrogeneous fertilizer.

10. The method defined in claim 9, wherein the composition is mixed with up to about an equal weight of a compound selected from the group consisting of ammonia, urea, ammonium nitrate, and mixtures thereof.

11. A method for inhibiting nitrification in soil, which comprises applying to the soil a composition comprising an aqueous solution containing from about 0.1 percent to about 50 percent by weight of a solute which comprises ammonium sulfide, carbon disulfide and a soluble sulfide, wherein the molarity of ammonium sulfide is equal to or greater than the molarity of carbon disulfide, and the combined molarity of ammonium sulfide and soluble sulfide is up to about twice the molarity of carbon disulfide.

12. The method defined in claim 11, wherein said soluble sulfide is selected from the group consisting of alkali metal sulfide, alkaline earth metal sulfide, and mixtures thereof.

13. The method defined in claim 11, wherein said solute further includes sulfur, in an amount up to about twice the molarity of carbon disulfide.

14. The method defined in claim 13, wherein the molarity of sulfur is equal to or greater than the molarity of carbon disulfide.

15. The method defined in claim 13, wherein carbon disulfide in the composition comprises up to about 20 percent by weight.

16. The method defined in claim 11, wherein carbon disulfide in the composition comprises up to about 25 percent by weight.

17. The method defined in claim 11, wherein the composition is mixed with up to about an equal weight of a compound selected from the group consisting of ammonia, urea, ammonium nitrate, and mixtures thereof.

* * * * *